United States Patent
Lemp et al.

(10) Patent No.: US 9,884,837 B2
(45) Date of Patent: Feb. 6, 2018

(54) METHOD FOR OBTAINING PHYTOSTEROLS AND/OR TOCOPHEROLS FROM RESIDUE OF A DISTILLATION OF THE ESTERS OF VEGETABLE OILS, PREFERABLY FROM DISTILLATION RESIDUE FROM A TRANSESTERIFICATION OF VEGETABLE OILS

(75) Inventors: Joachim Lemp, Delitzsch (DE); Nico Baade, Aschersleben / OT Schackstedt (DE); Emanuel Pöhls, Leipzig (DE)

(73) Assignee: VERBIO VEREINIGTE BIOENERGIE AG, Leipzig (DE)

( * ) Notice: Subject to any disclaimer, the term of this patent is extended or adjusted under 35 U.S.C. 154(b) by 361 days.

(21) Appl. No.: 13/883,116

(22) PCT Filed: Nov. 2, 2011

(86) PCT No.: PCT/EP2011/069236
§ 371 (c)(1),
(2), (4) Date: Jul. 2, 2013

(87) PCT Pub. No.: WO2012/059512
PCT Pub. Date: May 10, 2012

(65) Prior Publication Data
US 2013/0274489 A1   Oct. 17, 2013

(30) Foreign Application Priority Data
Nov. 3, 2010   (DE) .......... 10 2010 050 293

(51) Int. Cl.
C07J 9/00        (2006.01)
C07D 311/72      (2006.01)
C07D 311/58      (2006.01)
C11C 3/00        (2006.01)

(52) U.S. Cl.
CPC .......... *C07D 311/58* (2013.01); *C07D 311/72* (2013.01); *C07J 9/00* (2013.01); *C11C 3/003* (2013.01); *Y02E 50/13* (2013.01)

(58) Field of Classification Search
CPC ........ C07D 311/72; C11C 3/003; Y02E 50/13
USPC .......................................... 552/545; 549/413
See application file for complete search history.

(56) References Cited

U.S. PATENT DOCUMENTS

| | | | |
|---|---|---|---|
| 3,335,154 A | 8/1967 | Smith | |
| 3,887,537 A | 6/1975 | Harada et al. | |
| 5,424,457 A | 6/1995 | Sumner, Jr. et al. | |
| 5,627,289 A | 5/1997 | Jeromin et al. | |
| 6,780,831 B2 | 8/2004 | Hamunen | |
| 6,815,551 B2 | 11/2004 | Albiez et al. | |
| 2002/0058827 A1 | 5/2002 | Wollmann et al. | |
| 2002/0082431 A1 | 6/2002 | Cornille et al. | |
| 2002/0082434 A1 | 6/2002 | Bonakdar et al. | |
| 2005/0033027 A1 | 2/2005 | Rohr et al. | |
| 2008/0015367 A1 | 1/2008 | Dobbins et al. | |

FOREIGN PATENT DOCUMENTS

| | | |
|---|---|---|
| DE | 4228476 A1 | 3/1994 |
| DE | 10038456 A1 | 2/2002 |
| DE | 10038457 A1 | 2/2002 |
| EP | 0952208 A2 | 10/1999 |
| EP | 1081156 A2 | 3/2001 |
| EP | 1 179 535 A1 | 2/2002 |
| EP | 1 179 536 A2 | 2/2002 |
| EP | 0 656 894 B2 | 6/2002 |
| EP | 1 226 157 A1 | 7/2002 |
| EP | 1586624 A1 | 10/2005 |
| WO | 9916785 A1 | 4/1999 |
| WO | 9942471 A1 | 8/1999 |
| WO | WO-2005/051294 A2 | 6/2005 |

OTHER PUBLICATIONS

International Search Report (in German with English translation) for PCT/EP2011/069236, dated Jan. 17, 2012; ISA/EP.
Third Party Observations filed on Oct. 17, 2016, in connection with European Patent Application No. 20110784965, a European counterpart to the present application.

*Primary Examiner* — Barbara P Badio
(74) *Attorney, Agent, or Firm* — Kriegsman & Kriegsman

(57) ABSTRACT

The invention relates to a method for obtaining and purifying phytosterols and/or tocopherols from distillation residue from a transesterification of vegetable oils, in particular from the vegetable oil-based fatty acid methyl ester production for the field of use of biodiesel (FAME), comprising a first transesterification stage for converting partial glycerides contained in the distillation residue; separating the glycerin phase from a reaction mixture resulting from the first transesterification stage; a second transesterification stage for converting sterol esters contained in the reaction mixture; adding water to the reaction mixture after the second transesterification stage in order to generate a multiphase system; simultaneously or sequentially separating the phases of the multiphase system into a substantially sterol-containing phase; a substantially glycerin- and methanol-containing aqueous phase; and a tocopherol-containing methyl ester phase; and obtaining phytosterols from the sterol-containing phase; and optionally obtaining tocopherols from the tocopherol-containing methyl ester phase. The invention further relates to a method for purifying a phytosterol phase and/or phytosterols.

25 Claims, No Drawings

METHOD FOR OBTAINING PHYTOSTEROLS AND/OR TOCOPHEROLS FROM RESIDUE OF A DISTILLATION OF THE ESTERS OF VEGETABLE OILS, PREFERABLY FROM DISTILLATION RESIDUE FROM A TRANSESTERIFICATION OF VEGETABLE OILS

CROSS-REFERENCE TO RELATED APPLICATIONS

This application is a 371 U.S. National Stage of International Application No. PCT/EP2011/069236, filed on Nov. 2, 2011, which claims priority to German Patent Application No. 102010050293.6, filed Nov. 3, 2010, the contents of which are hereby incorporated by reference in their entirety as if fully set forth herein.

The invention relates to a method of obtaining phytosterols and/or tocopherols from residues of a distillation of the esters of vegetable oils, preferably from distillation residues from a transesterification of vegetable oils and also to a method of purification of a sterol-containing phase, in particular sterol crystals.

The main sources of phytosterols nowadays are residues from tall oil processing and steamer distillates from vegetable oil refining, and there are a few method patents on the basis of these raw materials. A further, hitherto hardly exploited source for obtaining phytosterols and tocopherols consists of distillation residues from the vegetable oil methyl ester production for the field of use of biodiesel (FAME). Accordingly few methods are known.

Basically, with distillation residues from the vegetable oil methyl ester production care should be taken to ensure that the matrix of concomitant components and contaminants, which can have a disruptive effect on the process for obtaining sterols and tocopherols with regard to achievable yields and purities, is different from the one in steamer distillates. Mention may be made at this point by way of example of phosphatides, colouring components, enriched long-chain fatty acid methyl esters and polymerisation products from the distillation, which are to be found in the residue. In this respect methods tailored to the treatment of steamer distillates cannot be used for distillation residues with satisfactory results.

In EP 0 656 894 B2 a method is described which makes it possible to simultaneously obtain phases containing sterols or tocopherols from residues from the production of rapeseed oil methyl ester (RME). The method is characterised by a single-stage basically catalysed transesterification with 50% by weight to 60% by weight of a lower alcohol, preferably methanol, at temperatures of 60° C. to 90° C. with 0.8% by weight to 1.5% by weight catalyst, preferably sodium methylate, followed by a separation off of the excess alcohol by distillation and a separation off of the catalyst-containing glycerin phase. By acidification to the neutral point and subsequent washing with water the catalyst and glycerin residues remaining in the ester phase and the formed alkali soaps are removed. Then the alkyl ester is separated out by distillation from the ester phase containing sterols and tocopherols. Out of the distillation residue the sterols can be separated from the tocopherols by means of crystallisation, and the sterol crystallisate is washed with methanol.

However, the crystallisation of the sterols out of a matrix which is largely free of alkyl ester and alcohol, coupled with the non-optimal reactions of the sterols in the single-stage transesterification, causes insufficient yields and purities of the sterols obtained by means of this method.

A method described in EP 1 179 535 (2001) and in EP 1 179 536 (2001) constitutes a further development. Sterol-rich residues from the distillation of transesterified oils of vegetable origin (FAME) are subjected to a two-stage basically catalysed transesterification with short-chain alcohols, preferably methanol, at temperatures in the range from 115° C. to 145° C. In the first stage with 0.5% by weight to 1.8% by weight catalyst and 5% by weight to 40% by weight methanol a thorough conversion of the partial glycerides to fatty acid alkyl esters takes place, whilst in the second stage the transformation of sterols into free sterols and fatty acid alkyl esters takes place under more stringent conditions with 1.8% by weight to 6% by weight catalyst and 40% by weight to 80% by weight methanol. It is also characteristic of the method according to the aforementioned documents that after each stage the basic catalyst must be neutralised by the addition of acid, the excess alcohol must be flashed off and then catalyst and formed reaction glycerin must be separated off by washing with water. Moreover the fatty acid alkyl ester must be distilled off for concentration of the sterols in the mixture after the first stage. The free sterols are crystallised out following the transesterification by cooling of the batch to approximately 20° C. and the crystallisate thus obtained is purified by means of washing, not described in greater detail, with solvent. The purity of the sterols thus obtained is given as >90%, but the yield, in spite of recycling of mother liquor in the crystallisation, at somewhat over 50% is not satisfactory.

It is also a disadvantage of the method as described in EP 1 179 535 and in EP 1 179 536 that the method necessitates high transesterification temperatures in the pressurised reactor, long reaction times of more than 4 to 8 hours, high alcohol and catalyst dosages, flashing off and new dosaging of the alcohol, addition of acid for neutralisation of the catalyst and distillation off of the fatty acid alkyl ester—in order to be added later again as solvent for phase separation/support for the crystallisation. This all gives rise to high operating costs and an expensive and complicated conduct of the method. Moreover the method is not designed for simultaneously obtaining a tocopherol-rich phase.

A further different method concept is set out in EP 1 226 157 (2000). After a single-stage basically catalysed transesterification of a residue from the methyl ester distillation, without a further flash or distillation step water is added into the raw ester, which accordingly still contains catalyst and a quantity of methanol necessary for the method. Two phases are formed, wherein the lower aqueous phase which also contains methanol and catalyst is separated off and then the upper oily phase which contains methyl ester and free and esterified sterols is cooled to temperatures preferably between 1° C. and 20° C. The sterol crystals which are formed in this case in the oil phase are separated off and for purification are subjected to a recrystallisation in methanol and subsequent drying. The addition of water in the presence of the methanol should produce a higher purity of the sterols obtained, but this does not exceed 70% in spite of recrystallisation. Even if this is preceded by a separation off, which is necessary according to the method, of high-melting fatty acid methyl ester from the transesterified batch by a methyl ester content >20%, exceeds the sterol purity there does not exceed 90% and the yield does not exceed 70%.

The comparatively high methanol dosage of over 100% by weight, based on the distillation residue, and the high water dosage according to the method of 55% and more, based on the quantity of methanol present in the batch, which are necessary there, since otherwise no heavy phase forms, lead to high operating costs. According to the method the separation off of the heavier water phase precedes the separation off of the sterol crystals from the oily phase, which necessitates an additional method step. The two crystallisation steps which are additionally necessary, namely a preliminary separation off of the high-melting methyl ester and a recrystallisation of the sterol crystallisate, also impair the economy of the method. Moreover this method is not directed to simultaneously obtaining tocopherols.

U.S. Pat. No. 3,335,154 already reports on the effect of the crystallisation out of sterols from a fatty acid alkyl ester/alkyl alcohol matrix following an acidically catalysed esterification of steamer distillates originating from vegetable oil by the addition of sufficient water and cooling of the batch to below 40° C. In a first method step the fatty acids present in the starting material together with the partial glycerides and sterol esters are complete saponified, the fatty acid alkali soaps are then split again by the addition of acid, in order then to carry out the esterification of the released fatty acids to methyl esters which acidic catalysis. By the addition of 5% by weight to 60% by weight water in the reaction mixture and cooling to a temperature between 0° C. and 40° C. the sterols crystallise out. According to the invention the crystallisate is separated out of the suspension and purified by washing with polar solvents.

The steps of saponification/soap splitting circumvent the disadvantage of the substantially poorer reaction kinetics of an acidically catalysed transesterification by comparison with a basically catalysed transesterification, achieved by a very high acid/base requirement according to the method (20% by weight of a 50% sodium hydroxide solution and a correspondingly super-stoichiometric quantity of HCl). Furthermore a total of 120% by weight of methanol based on the starting material are used for saponification and esterification. For residues from the vegetable oil methyl ester production, which generally only have lowest amounts of fatty acids but high contents of methyl esters, this method is complex and uneconomical by comparison with basically catalysed transesterification.

The method employed there uses the effect of simplified phase separation in a suspension/emulsion of water phase, methyl ester phase and sterol crystals in an acidic medium, nevertheless the purity of the sterol crystals is insufficient even after intensive washing with polar solvents, which is why according to the invention an additional recrystallisation or solvent extraction with hexane must be provided afterwards.

Furthermore a more recent method for obtaining sterols from steamer distillates is described in U.S. Pat. No. 5,424,457. It is characterised by transesterification/esterification, catalysed with an alkyl tin, in particular dibutyl tin oxide, of the sterol esters, partial glycerides and fatty acids with methanol at temperatures from 150° C. to 240° C., for example at 200° C., with the addition of glycerin, followed by a separation off of the excess methanol and the reaction water by distillation and a filtration of the batch at 100° C. for separation off of secondary reaction products or precipitated catalyst fractions. After separation off of the catalyst-containing glycerin phase the remaining sterol-containing filtrate phase is again mixed at 70° C. with approximately 16% of a methanol/water mixture (3:1). With cooling to 25° C. the sterols in the methyl ester/methanol/water matrix then crystallise out. The sterol crystallisate is filtered off and while undergoing redispersion is washed intensively with solvent, namely heptane cooled to 5° C.

Since the method according to U.S. Pat. No. 5,424,457, starting from steamer distillate as sterol-containing raw material, is not directed to the integration into a biodiesel plant, a type of catalyst is used which is disadvantageous in the FAME production because of the costs and reaction conditions. In particular the problem of a potential tin loading of the end product set out in the patent militates against a use of the sterols obtained by means of this method in the food sector. The large amounts of cooled solvent, of over 1000% based on the sterols obtained, which are necessary according to the embodiment for washing the crystallisate are disadvantageous. The purity of the sterols given as 98% is worthy of note, but the further statements show that the achievable yields in favour of lower tin contents in the end product fall significantly below 70%. Furthermore the handling or the disposal of the secondary reaction products filtered off after the method step of removing the excess methanol and the glycerin phase which is highly contaminated with tin should be regarded as disadvantageous.

The object of the invention is to avoid the aforesaid disadvantages and to provide a simple and cost-effective method for obtaining free sterols and/or tocopherols, in each case with a high degree of purity and in each case with a high yield of distillation residues from biodiesel production (=FAME production), wherein this method is particularly economical due to a few method steps and the use of substances which are usual in FAME plants as reagents and by means of a resulting full implementation in a FAME plant.

In particular the object is achieved by a method for obtaining phytosterols and/or tocopherols from residues of a distillation of the esters of vegetable fatty acids and/or oils, preferably from distillation residues from a transesterification of vegetable oils, in particular from the vegetable oil-based fatty acid methyl ester production for the biodiesel (FAME) field of use, wherein the method comprises a two-stage basically catalysed transesterification with an interposed separation off of the glycerin phase, wherein in particular in a first basic transesterification stage an at least far-reaching reaction of partial glyceride contained in the distillation residues is carried out;

glycerin phase is separated off from a reaction mixture directly resulting from the first basic transesterification stage without any further method step;

in a second basic transesterification stage an at least far-reaching reaction of sterol esters contained in the reaction mixture is carried out.

According to a preferred and particularly advantageous embodiment of the invention water is added to the reaction mixture after the second transesterification stage in order to produce a multi-phase system. Following this according to the invention the phases of the multi-phase system are simultaneously or sequentially separated into a substantially sterol-containing phase;

a substantially glycerin-containing and methanol-containing aqueous phase; and a tocopherol-containing methyl ester phase; and obtaining phytosterols from the sterol-containing phase; and/or if appropriate, obtaining tocopherols from the tocopherol-containing methyl ester phase.

A significant point of the invention is that the method according to the invention consisting of a two-stage basically catalysed transesterification of a fatty acid methyl ester distillation residue (=FAME distillation residue) from the biodiesel production with an intermediate separation off of a glycerin phase produced in the transesterification accrue for completion of the glyceride reaction is carried out in the second reaction stage without methanol or catalyst having to be removed by flashing, distillation or washing.

Thus according to the invention and in an advantageous manner a reaction mixture from the first transesterification stage can be further processed directly in a second transesterification stage, wherein before a stage in which the phases of the multi-phase system produced according to the invention are separated in any case it is not necessary to remove methanol or catalyst from the reaction mixture. Thus according to the invention with this procedure it is not only possible to operate very economically and simply but also the degrees of reaction are so good that results in terms of yield and purity which were not achieved hitherto can be achieved when the reaction mixture is further processed.

The glycerin phase produced after the first transesterification stage can advantageously be fed directly to a process for obtaining glycerin associated with a biodiesel production process.

The method according to the invention is also carried out so that the first and/or the second transesterification stage is carried out at a temperature in the range from room temperature (=25° C.) to 88° C., preferably in the range from 40° C. to 75° C. and particularly preferably in the range from 55° C. to 70° C., and furthermore in particular at normal pressure. This embodiment of the invention enables an energy-saving and cost-efficient conduct of the method, since high heating costs are avoided and the respective transesterification reactions can be carried out inter alia at normal pressure, so that according to the invention expensive pressurised reactors and complex and expensive generation and maintenance of the temperatures and pressures, such as are necessary in the prior art, can be omitted.

Furthermore, the low reaction temperature during the first and/or the second transesterification stage contributes to a significant reduction in the operating costs relative to known methods and thus also crucially improves the economy of the method relative to previously customary methods.

A further advantage of the transesterification which can be carried out according to the invention without pressure also resides in the fact that costly safety measures, which are necessary in the event of the use of pressure vessels, can be omitted when the method according to the invention is applied, since all operations are carried out at normal or atmospheric pressure, and, due to the low reaction temperatures, in an energy-efficient manner and quickly.

According to the invention the first transesterification stage is carried out with a content of basic catalyst, preferably sodium methylate, but for example also sodium hydroxide (NaOH) or potassium hydroxide (KOH), in the range from 0.1% to 0.3%, preferably in the range from 0.18% to 0.22% and with a methanol content in the range from 12% to 18%, preferably in the range from 14% to 16% and the second transesterification stage with a content of catalyst in the range from 0.5% to 1%, preferably in the range from 0.6% to 0.8% and with a methanol content in the range from 20% to 38%, preferably in the range from 34% to 36%, wherein the added quantity of basic catalyst is standardised to an addition of sodium methylate and if appropriate should be adapted to use of other basic catalysts. On the basis of these necessary additions of catalyst and methanol, which were very low with regard to known methods, to the individual transesterification stages the method according to the invention can be operated in a particularly cost-effective and recycling-friendly manner, since for example only small quantities of methanol must be supplied for methanol recovery.

Moreover the basic catalyst used according to the invention can be used and recycled without any environmental or food-related problems, wherein in an advantageous manner, unlike for example in the aforesaid U.S. Pat. No. 5,424,457, there should be no fear of heavy metal contamination in the produced products, in this case phytosterols and/or tocopherols.

According to a preferred embodiment, when water is added it is added in an amount in the range from 15% to 25%, preferably from 18% to 22% and particularly preferably in the range from 19.5% to 20.5%, in each case based on the mass of a total batch, in order in particular to set a mass ratio of sterol:fatty acid methyl esters:methanol:water of substantially 1:2.5-3:2.2-2.5:0.8-1.2.

The addition of water to the reaction mixture, which according to the invention takes place after the second transesterification stage, makes it possible in a particularly simply manner for substances which would impede crystallisation of the sterols to be removed in particular from a sterol-containing phase of the transesterified batch. Thus by the addition of water glycerin present in the reaction mixture, catalyst and contaminants are separated off from the distillation residue, wherein the said substances pass into the water phase. Furthermore the added water largely extracts the methanol which is still present in the reaction mixture, so that the solubility of the sterols in the methyl ester phase decreases considerably and they crystallise out.

Furthermore during the addition of water to the reaction mixture it was surprisingly ascertained that when a specific water concentration is reached a spontaneous, very complete crystallisation out of the sterols can already be observed at the reaction temperature, wherein a 3-phase system, consisting of a fatty acid methyl ester phase, a water phase and sterol crystals forms simultaneously, wherein the respective density of the three phases increases in the aforesaid sequence. Thus it has been shown that in particular the addition in the aforesaid quantitative ratio of sterol:fatty acid methyl esters:methanol:water of substantially 1:2.5-3:2.2-2.5:0.9-1.1 is particularly effective in order to achieve a clear separation of the three phases, whereby further processing of the reaction mixture is greatly simplified, which in turn has an extremely positive effect on the economy of the procedure, in particular with regard to an energy-saving and time-saving reaction of the starting products and obtaining the desired phytosterols and tocopherols.

According to a further embodiment of the invention, during the first transesterification stage after mixing in of methanol and catalyst glycerin is added in an amount in the range from 0.2% to 7.2%, preferably in the range from 0.5% to 6.0% and particularly preferably in the range from 1.0% to 5.5%, in each case based on the mass of the total batch. By this addition of glycerin to the total batch according to the invention the later phase separation is improved and contaminants are better discharged in an advantageous manner into the heavy glycerin phase.

Furthermore during a preferred embodiment of the invention the distillation residue from a transesterification of vegetable oils is adjusted by an addition of fatty acid methyl ester before the first and/or second transesterification stage so that a solubility of the sterols during the transesterification is ensured and is maintained, so that according to the invention the sterols are not precipitated already at the first and/or second transesterification stage in an uncontrolled manner but remain in the solution in a controlled manner.

Moreover the parameters of the transesterification, in particular the dosage of the basic catalyst and the reaction temperatures, are chosen according to the invention so that a maximum conversion of the partial glycerides or sterol esters is achieved whilst the tocopherols present in the distillation residue are largely unaffected.

According to a further advantageous embodiment the reaction mixture is homogenised by mixing to an emulsion or a suspension, in particular after the addition by water in the mass ratios defined above. This constant thorough intermixing of the reaction mixture prevents sedimentation of sterol crystals already formed after the addition of water, wherein the homogenisation assists the crystallisation process of the phytosterol crystals and a crystal formation which is optimised for the further processing.

Furthermore it has proved advantageous to cool the homogenised emulsion or suspension to a temperature in the range from 5° C. to 35° C., preferably in the range from 10° C. to 30° C. and particularly preferably in the range from 15° C. to 25° C., so that a subsequent phase separation is simplified considerably. Furthermore the crystal structure of the required phytosterol crystals can be significantly improved by compliance with a maturation period, which in turn has a perceptible positive effect on improved filtration properties of the crystals and also yields of crystals. According to the invention the maturation period is in particular in the range from 1 hour to 48 hours, preferably in the range from 2 hours to 36 hours and particularly preferably in the range from 4 hours to 12 hours.

The separation of the phases is carried out according to the invention by means of a filter, screen or decanter centrifuge, wherein a filter centrifuge is preferably used. By the use of a filter or decanter centrifuge in practice a filter cake can be obtained with a significantly lower residual moisture than would be possible for example with differential pressure filtration.

Furthermore a 3-phase decanter is also very suitable for separating the multi-phase system according to the invention consisting of sterol-containing phase, glycerin-containing and methanol-containing phase and tocopherol-containing phase, wherein the phase containing sterol crystals or the sterol crystals themselves form the heaviest phase and can be separated off or pre-thickened well by means of the 3-phase decanter, whilst simultaneously the fatty acid methyl ester phase and the water phase containing glycerin and methanol can be obtained separately.

In this case the separation off of the sterol crystals by means of a discontinuously operating filter centrifuge also offers the possibility of carrying out cake washing immediately after the filtration.

The sterol-containing phase, which primarily contains sterol crystals, will subsequently washed with methanol, wherein the quantity of methanol is in the range from 50% to 800%, preferably in the range from 125% to 700% and particularly preferably in the range from 200% to 550%, in each case based on the mass of the sterol crystal phase. By the application of this methanol washing which is simple to carry out it is possible to eliminate any remaining residues of fatty acid methyl ester phase and water phase which may remain on the sterol crystals and in this way to separate the sterol crystals efficiently from the wedge fluid consisting of fatty acid methyl ester phase and water phase and in this way to purify the sterol crystals. The washing methanol resulting from this methanol washing can then be fed without further purification, in particular without rectification, to the process for biodiesel production.

Furthermore the objet according to the invention is achieved by the use of a method that enables the production of highly purified sterol crystals, and it should be emphasised that this purification method, according to the invention, is outstandingly suitable for use not only during the distillation residue processing according to the invention, but also explicitly in general for purification of sterol crystal phases and/or sterol crystals.

Accordingly the methanol washing may optionally also be preceded by displacement washing on the sterol filter cake with fatty acid methyl ester, preferably but not exclusively of the same type from which the distillation residue originates, that is to say for example rapeseed methyl ester if the distillation residue from the rapeseed methyl ester production is processed. In addition or alternatively other fatty acid methyl esters, such as for example soya and/or sunflower and/or coconut and/or palm and/or cottonseed oil and/or corn oil methyl ester, can be used for such displacement washing if this is required. Use of these esters or mixtures of these esters may be advantageous for example with regard to cost aspects, but also with regard to adjustability of solvent properties of the fatty acid methyl ester used for the displacement washing, for example with regard to any contaminants, possibly due to their origin, of the raw materials used. The quality of the crystallisate, in particular the purity and colour thereof, can also be significantly improved by this preceding displacement washing with methyl ester. The methyl ester which is more viscous by comparison with methanol is able to displace the wedge fluid from the filtration of the reaction mixture which remains in the sterol crystallisate and also any contaminants contained in the wedge fluid. Because of the lower polarity of the methyl ester this latter is also able to detach specific contaminants adhering on the sterol crystals which can only be removed to some extent by simple methanol washing. Due to the short action time of the displacement washing the sterol losses can be reduced to a minimum by re-dissolving in the methyl ester.

The aforementioned displacement washing with methyl ester is carried out according to the invention preferably with a quantitative ratio in the range from 15% to 500%, preferably in the range from 75% to 400% and particularly preferably in the range from 100% to 350%, in each case based on the mass of the sterol crystal phase, in order to adapt the purity and the colour of the sterol crystals to a desired level.

The crystallisate obtained in this way according to the invention from phytosterols can be dried immediately after the methanol washing in order in this way to obtain a free-flowing powder which can be packaged without further treatment, in particular without the need for further purification or recrystallisation.

Thus in the method according to the invention, unlike methods known from the prior art, sterol crystals are obtained without further purification, in particular without recrystallisation, which again contributes to the special economy and efficiency of the method according to the invention relative to already known generic methods according to the prior art.

Furthermore, by the use of the method according to the invention phytosterols can be obtained from the distillation residues from transesterification of vegetable oils with a purity of over 95% with yields of over 80%, which with regard to both purity and yield is significantly higher than with methods known from the prior art.

During a further stage of obtaining tocopherols from the tocopherol-containing phase the fatty acid methyl ester phase of the multi-phase system, which contains the tocopherol in dissolved form, is preferably subjected to a distillation for separation off of the methyl ester, whereby it is possible to concentrate the tocopherol content in the fatty acid methyl ester phase to over 10%, in order to enable a simple further preparation of the tocopherols in a known manner.

It should also be mentioned at this point that the fatty acid methyl ester separated off in the aforesaid distillation can be used again directly for adjusting the consistency of the residue from the biodiesel distillation according to a first optional method step. Furthermore it is possible to add distillate obtained from the biodiesel distillation directly to this fatty acid methyl ester, which again further improves the economy of the method according to the invention. In this connection it should also be pointed out that the water phase containing glycerin and methanol can be supplied to a methanol recovery system in a biodiesel plant, wherein the method can be carried out very simply and cost-effectively because of the specifically low amount of water phase produced according to the invention. It is also worth mentioning at this point that the water dosage according to the invention is chosen so that crystals form with such a size that they can be easily precipitated and/or filtered, wherein a higher water dosage would lead to smaller crystals which are therefore more difficult to precipitate or filter. An addition of less water to the reaction mixture would on the other hand lead to a decrease in the density of the water phase, which again would mean poorer results in the phase separation and thus also a poorer yield.

Thus the method according to the invention can be implemented completely in an advantageous manner in a process for production of biodiesel, wherein only catalyst, methanol and water are necessary, in each case in amounts significantly lower than in the previous prior art, which on the one hand enables a cost-effective conduct of the method and on the other hand reduces the cost of methanol recovery. Furthermore, in the method according to the invention no recrystallisation of the phytosterol crystals obtained is necessary, and it is also possible to dispense with the use of solvents which are to be regenerated separately, such as e.g. acetone, hydrocarbons etc., as washing medium, wherein the amount of washing medium according to the invention is significantly lower than in other methods and the washing methanol used can advantageously be further used directly in a process for biodiesel production. Furthermore the crystallisation batch can actually be cooled to temperatures up to 5° C.; however, according to the invention it is not absolutely necessary to cool the crystallisation batch to a temperature below 20° C. Furthermore in spite of an up to 20% fatty acid methyl ester fraction in the transesterified batch no preliminary separation off of high-melting methyl ester is necessary. A further important advantage of the method according to the invention also resides in the possible simple use of a 3-phase decanter, in order to separate off the phytosterol crystals as heaviest phase from the multi-phase mixture according to the invention. Furthermore an almost complete recovery of the tocopherols contained in the distillation residue is possible.

Thus to summarise it may be noted that by means of the method according to the invention, which is characterised in particular by a two-stage basically catalysed transesterification with a glycerin phase precipitation after the first transesterification stage and then sterol crystallisation out of the reaction mixture with the addition of water, wherein interposed method steps such as neutralisation, distillation off of reagents or solvents and washing out of catalyst are omitted, and in which furthermore by means of a combination of methyl ester displacement washing followed by methanol washing of the sterol crystallisate filter cake whilst adhering to specific aforesaid process parameters it is possible to obtain phytosterols and tocopherols from distillation residues from a transesterification of vegetable oils, in particular from the vegetable oil-based fatty acid methyl ester production for the field of use of biodiesel with levels of purity and yield which have not been attained hitherto. Furthermore the previously described method according to the invention can be fully implemented in a plant for FAME production, wherein in an advantageous manner according to the invention the substances which are usual in FAME plants can be used in an optimal manner as reagents, which is why the method is particularly effective and economical both from the economical point of view and also from the logistical aspects.

Further embodiments of the invention are set out in the subordinate claims.

The invention is explained in greater detail below with reference to embodiments.

EMBODIMENT 1

3850 g of a residue from the distillation of rapeseed methyl ester were mixed according to the invention with 1782 g RME. The analysis of the batch gave contents of 21.73% sterol ester, 6.21% free sterols, 1.68% tocopherols, 9.8% glycerides and 44.17% methyl ester.

The batch was temperature-controlled at 65° C. and in a first transesterification stage 37.5 g Na methylate (30% solution in methanol) and 818 g methanol were added and mixed in. After 50 minutes settling time 301.2 g glycerin-containing bottom phase were drawn off. The reaction in the partial glycerides was over 95%.

For the second transesterification stage for conversion of the sterol esters into free sterols 150.2 g Na methylate (30% solution in methanol) and 1865.6 g methanol were added. The reaction took place at 65° C. over 90 minutes.

1126 g water were added to the batch whilst being stirred, and sterol crystals formed. The suspension was cooled to 20° C. whilst being stirred and then subjected to maturation at this temperature.

Then the suspension was filtered by means of a filter centrifuge, and the cake formed was subjected while still in the centrifuge to a first washing with 3.5 liters RME distillate and a second washing with 10.4 liters methanol. After drying of the filter cake moistened with methanol the result was 908 g of white sterol powder with a sterol content of over 98%, which corresponds to a yield (based on the total sterol content of the distillation residue) of over 82%.

The filtrate from the filtration of the suspension separated automatically into a light phase containing methyl esters, sterols and tocopherols and into an aqueous phase containing methanol and catalyst. Sterols and tocopherols were also dissolved in the washing RME phase, whilst no tocopherols were detectable in the washing methanol phase.

In the combined methyl ester phases there were 87% of the tocopherols originally detected in the RME distillation residue. After distillation of the methyl ester phases a residue with a tocopherol content of 11% could be obtained which is suitable for further working up of the tocopherols.

EMBODIMENT 2

3119 g of a residue from the distillation of rapeseed methyl ester were mixed according to the invention with 2324 g RME. The analysis of the batch gave contents of 27.2% sterol ester, 5.17% free sterols, 1.12% tocopherols, 8.14% glycerides and 42.74% methyl ester.

The batch was temperature-controlled at 65° C. and in a first transesterification stage 36.3 g Na methylate (30% solution in methanol) and 873.5 g methanol were added and mixed in. After 50 minutes settling time 319.2 g glycerin-containing bottom phase were drawn off. The reaction in the partial glycerides was over 95%.

For the second transesterification stage for conversion of the sterol esters into free sterols 145.1 g Na methylate (30% solution in methanol) and 1995.7 g methanol were added. The reaction took place at 65° C. over 90 minutes.

1208 g water were added to the batch whilst being stirred, and sterol crystals formed. The suspension was cooled to 20° C. whilst being stirred and then subjected to maturation at this temperature.

Then the suspension was filtered by means of a filter centrifuge, and the cake formed was subjected while still in the centrifuge to a first washing with 2.4 liters RME and a second washing with 10.4 liters methanol. After drying of the filter cake moistened with methanol the result was 956 g of white sterol powder with a sterol content of over 98%, which corresponds to a yield (based on the total sterol content of the distillation residue) of 80%.

If required, the concentrated methyl ester phase can be further used within the context of a new transesterification and crystallisation.

According to a further exemplary embodiment of the method according to the invention, in a first step the consistency of a distillation residue from the transesterification of vegetable oils for the production of biodiesel is adjusted by the addition of fatty acid methyl ester for further processing in a first transesterification stage, wherein so much fatty acid methyl ester is added to the distillation residue that the solubility of the sterols contained in the distillation residue is maintained during the subsequent transesterification. Then in a first transesterification stage with a content of 0.2% catalyst, namely sodium methylate, and 15% methanol a reaction of the partial glycerides from the distillation residue is carried out, wherein after the addition of the catalyst and of the methanol 1% to 5% glycerin are also added for improvement of a later phase separation. Next the glycerin phase which has formed in the reaction mixture is separated off, wherein contaminants, in particular phosphatides, are discharged into the glycerin phase. Following this a second transesterification stage is carried out with the remaining reaction mixture, wherein 0.8% catalyst and 35% methanol are now contained in the reaction mixture or if need be are supplemented to this proportion. A preceding separation off of catalyst and methanol after the first transesterification stage is not necessary in this case. After the second transesterification stage, which like the first transesterification stage is carried out at a temperature of 65° C. at atmospheric pressure, in order to effect a crystallisation of the phytosterols contained in the reaction mixture approximately 20% by volume of water is added to the reaction mixture, so that a multi-phase system is produced consisting of sterol crystal phase, a glycerin-containing and methanol-containing aqueous phase and a tocopherol-containing fatty acid methyl ester phase. The phytosterol crystals are separated out of this multi-phase system by centrifugation and filtration of the suspension and washed with 1 to 3 times the weight of rapeseed methyl ester in the context of displacement washing, which is followed by further washing with methanol in 2 to 5 times the weight of the crystallisate. After this methanol washing the crystallisate is dried and delivered for packaging. Further processing of the remaining reaction mixture takes place by a separation of the aqueous and the methyl ester phase, wherein the methyl ester phase is distilled for concentration of the tocopherol content distilled and in this way the methyl esters are largely separated off. The remaining tocopherol-rich methyl ester phase is then passed on for further processing and recovery of the tocopherols.

At this point it should be pointed out that all the parts described above, considered alone and in any combination, are claimed as essential to the invention. Modifications thereof are familiar to the person skilled in the art.

The invention claimed is:

1. A method of obtaining phytosterols and/or tocopherols from residues of a distillation of the esters of vegetable oils, wherein the method comprises a two-stage basic transesterification with an interposed separation of the glycerin phase, wherein
   in a first basic transesterification stage, a reaction of partial glycerides contained in the distillation residues is carried out, whereby a lower phase and an upper phase are formed, the lower phase comprising glycerin, the upper phase comprising catalyst and unreacted methanol;
   the lower phase comprising glycerin is separated from said upper phase; and
   without an interposing method step, a reaction of sterol esters contained in the upper phase is carried out in a second basic transesterification stage;
and wherein the method further comprises,
   after the second transesterification stage, adding water to a reaction mixture derived from the upper phase to crystallize sterols within the reaction mixture, the water being added in an amount ranging from 15% to 25% based on the mass of a total batch in order to set a mass ratio of sterol:fatty acid methyl esters:methanol:water of substantially 1:2.5-3:2.2-2.5:0.8-1.2;
   during and after the addition of water, homogenizing the reaction mixture to an emulsion/suspension by mixing, whereby a multi-phase system is produced, the multi-phase system comprising a methyl ester phase, an aqueous phase, and sterol crystals;
   then, separating the multi-phase system into a substantially sterol-containing phase, a substantially glycerin-containing and methanol-containing aqueous phase, and a tocopherol-containing methyl ester phase;
   then, obtaining phytosterols from the substantially sterol-containing phase; and/or
   obtaining tocopherols from the tocopherol-containing methyl ester phase.

2. The method as claimed in claim 1, wherein the first and/or the second transesterification stage is carried out at a temperature in the range from room temperature (25° C.) to 88° C. at normal or atmospheric pressure.

3. The method as claimed in claim 1, wherein the first transesterification stage is carried out with a content of catalyst in the range from 0.1% to 0.3% and with a methanol content in the range from 12% to 18% and the second transesterification stage is carried out with a content of catalyst in the range from 0.5% to 1% and with a methanol content in the range from 30% to 38% based on the mass of a total batch, wherein a basic catalyst is used as catalyst.

4. The method as claimed in claim 1, wherein during the first transesterification stage after addition of transesterification components methanol and catalyst glycerin is added in an amount in the range from 0.2% to 7.2% based on the mass of the total batch.

5. The method as claimed in claim 1, wherein the method further comprises cooling the emulsion/suspension to a temperature below a transesterification temperature to a temperature in the range from 5° C. to 35° C.

6. The method as claimed in claim 1, wherein the method further comprises cooling the emulsion/suspension is matured during a maturation period with a duration in the range from 1 hour to 48 hours.

7. The method as claimed in claim 1, wherein the separation of the phases is carried out by means of a filter, screen and/or decanter centrifuge.

8. The method as claimed in claim 1, wherein the sterol-containing phase primarily contains sterol crystals which are washed with methanol in a quantity in the range from 50% to 800% based on the mass of the sterol crystal phase, wherein this methanol washing is optionally preceded by a displacement washing of the sterol crystals with methyl ester, with a quantitative ratio in the range from 50% to 500% based on the mass of the sterol crystal phase.

9. The method as claimed in claim 8, wherein the sterol crystals are dried directly after the methanol washing and are then packaged without further treatment/purification.

10. The method as claimed in claim 1, wherein the substantially glycerin-containing and methanol-containing phase is supplied to a methanol recovery system and/or the washing methanol is supplied directly to a biodiesel plant.

11. The method as claimed in claim 1, wherein methyl ester is added to the distillation residue before the first and/or the second transesterification stage.

12. The method as claimed in claim 1, wherein the first and second transesterification stages are carried out at a temperature in the range from 40° C. to 70° C. at normal or atmospheric pressure.

13. The method as claimed in claim 1, wherein the first transesterification stage is carried out with a content of catalyst in the range from 0.18% to 0.22% and with a methanol content in the range from 14% to 16% and the second transesterification stage is carried out with a content of catalyst in the range from 0.6% to 0.8% and with a methanol content in the range from 34% to 36% based on the mass of a total batch, wherein a basic catalyst is used as catalyst.

14. The method as claimed in claim 3, wherein the basic catalyst is selected from the group consisting of sodium methylate, sodium hydroxide and/or potassium hydroxide.

15. The method as claimed in claim 1, wherein the water is added in an amount in the range from 18% to 22% based on the mass of a total batch.

16. The method as claimed in claim 1, wherein during the first transesterification stage after addition of transesterification components methanol and catalyst glycerin is added in an amount in the range from 0.5% to 6% based on the mass of the total batch.

17. The method as claimed in claim 1, wherein the method further comprises cooling the emulsion/suspension to a temperature below a transesterification temperature in the range from 10° C. to 30° C.

18. The method as claimed in claim 1, wherein the method further comprises maturing the emulsion/suspension during a maturation period with a duration in the range from 2 hours to 36 hours.

19. The method as claimed in claim 8, wherein the sterol-containing phase primarily contains sterol crystals which are washed with methanol in a quantity in the range from 125% to 700% based on the mass of the sterol crystal phase, wherein this methanol washing is optionally preceded by a displacement washing of the sterol crystals with methyl ester with a quantitative ratio in the range from 75% to 400% based on the mass of the sterol crystal phase.

20. The method as claimed in claim 8, wherein the methyl ester is vegetable oil methyl ester.

21. The method as claimed in claim 20, wherein the vegetable oil methyl ester is selected from the group consisting of rapeseed oil, soya oil, sunflower oil, coconut oil, palm oil, cottonseed oil, corn oil and combinations thereof.

22. The method as claimed in claim 20, wherein the vegetable oil methyl ester is selected from the group consisting of rapeseed oil, soya oil, sunflower oil, coconut oil, palm oil, cottonseed oil, corn oil and combinations thereof.

23. The method as claimed in claim 1, wherein phytosterols are obtained from the substantially sterol-containing phase.

24. The method as claimed in claim 1, wherein tocopherols are obtained from the tocopherol-containing methyl ester phase.

25. The method as claimed in claim 1, wherein phytosterols are obtained from the substantially sterol-containing phase and wherein tocopherols are obtained from the tocopherol-containing methyl ester phase.

* * * * *